United States Patent [19]

Livingston

[11] Patent Number: 4,642,380

[45] Date of Patent: Feb. 10, 1987

[54] PURIFICATION OF METHACRYLAMIDOPROPYLTRIMETHYLAMMONIUM CHLORIDE

[75] Inventor: David R. Livingston, Austin, Tex.

[73] Assignee: Texaco Inc., White Plains, N.Y.

[21] Appl. No.: 535,016

[22] Filed: Sep. 23, 1983

[51] Int. Cl.$^4$ .................................. C07C 103/44
[52] U.S. Cl. .................................................. 564/206
[58] Field of Search .................... 564/206, 437, 497

[56] References Cited

U.S. PATENT DOCUMENTS

| | | | |
|---|---|---|---|
| 2,744,938 | 5/1956 | Urban, Jr. | 564/437 X |
| 2,865,960 | 12/1958 | Shearer, Jr. et al. | 564/206 |
| 2,882,244 | 4/1959 | Milton | 564/497 X |
| 2,999,861 | 9/1961 | Fleck et al. | 564/497 X |
| 3,728,408 | 4/1973 | Tobias | 564/437 X |
| 3,891,708 | 6/1975 | Woodrum et al. | 564/497 |
| 3,907,891 | 9/1975 | Guilbault et al. | 260/561 N |
| 4,360,696 | 11/1982 | Richmond | 564/206 X |
| 4,375,558 | 3/1983 | McEntire et al. | 564/206 |

OTHER PUBLICATIONS

Wu et al., "Adsorption and Diffusion of $C_6$ and $C_8$ Hydrocarbons in Silicalite", AICHE Mtg., Orlando, Fla., Feb. 28–Mar. 3, 1982.

Burfield et al., "Dissicant Efficiency in Solvent Drying . . . ", J. Org. Chem., vol. 42, No. 18, 1977, pp. 3060–3065.

*Primary Examiner*—Robert V. Hines
*Attorney, Agent, or Firm*—Jack H. Park; Kenneth R. Priem

[57] ABSTRACT

Trace impurities such as allyl methacrylate and methacrylic acid are removed by contacting methacrylamidopropyltrimethylammonium chloride with a hydrophobic/organophilic microporous crystalline silica.

8 Claims, No Drawings

PURIFICATION OF METHACRYLAMIDOPROPYLTRIMETHYLAMMONIUM CHLORIDE

BACKGROUND OF THE INVENTION

1. Field of the Invention

This invention relates to the purification of methacrylamidopropyltrimethylammonium chloride (sometimes abbreviated herein as MAPTAC). More particularly, this invention relates to the use of a microporous crystalline silica for removing trace quantities of detrimental impurities from methylacrylamidopropyltrimethylammonium chloride.

2. Prior Art

Methylacrylamidopropyltrimethylammonium chloride is a cationic vinyl monomer that undergoes homo- and copolymerization to provide polymeric products containing pendant quaternary ammonium groups that are useful, for example, in liquid/solid separation processes relating to water pollution control, paper manufacturing, textile finishing, etc. However, the properties of the homopolymers and copolymers prepared from methacrylamidopropyltrimethylammonium chloride are adversely affected by the presence of even trace quantities of impurities such as allyl methacrylate, methacrylic acid, diphenyl amines, etc. that are formed or introduced during the synthesis of this material. For example, as little as ten parts per million of allylmethacrylate or 15 parts per million of the methyl ether of hydroquinone will adversely affect the properties of the polymers made from methacrylamidopropyltrimethylammonium cyloride.

Microporous crystalline silica is a known commerical product having a topological type of tetrahedral framework characterized by straight channels along a b-axis defined by 10 membered oxygen rings with an elliptical cross section of 5.7–5.8 Å by 5.1–5.2 Å. These channels are interconnected by zigzag channels along an a-axis also defined by 10 membered oxygen rings with a nearly circular cross section of 5.4±0.2 Å. These channels are accessible to molecules having a diameter up to 6 Å. A commercial material is available from Union Carbide Corporation under the tradename "Silicalite". The properties and characteristics of the microporous crystalline silica which is a hydrophobic/organophilic silica, are described in greater detail in a paper entitled "Adsorption and Diffusion of $C_6$ and $C_8$ Hydrocarbons in Silicalite" by Pingdong Wu et al. presented at the AIChE Orlando, Fla., Meeting of Feb. 28–Mar. 3, 1982.

Although methacrylamidopropyltrimethylammonium chloride can be purified by conventional techniques such as solvent extraction and crystallation, it can be done so only with appreciable difficulty requiring multiple processing steps and significant processing equipment.

It is also suggested in U.S. Pat. No. 3,907,891 to Guilbault et al. dated Sept. 23, 1975 that methacrylamidopropyltrimethylammonium chloride, in aqueous solution, can be purified by contacting the solution with activated carbon. Although this process gives reasonably satisfactory results, there is still need for improvement in purifying methacrylamidopropyltrimethylammonium chloride in aqueous solution. For example, comparatively high temperatures are required to regenerate the activated carbon. Also, the carbon particles tend to crush which can result in the plugging of flow lines and/or the presence of very fine carbon particles in the purified product.

SUMMARY OF THE INVENTION

The present invention is directed to the removal of impurities from methacrylamidopropyltrimethylammonium chloride by contacting the chloride, in aqueous solution, with hydrophobic/organophilic microporous crystalline silica for a period of time sufficient to significantly lower the impurities content. In another aspect, the present invention is directed to a method for regenerating spent microporous hydrophobic/organophilic crystalline silica used in purifying the chloride by contacting the spent silica with a $C_1$–$C_4$ aliphatic alcohol or a $C_5$–$C_8$ alkene at a temperature of about 50° to 200° for a period of time adequate to disengage the impurities from the spent silica (e.g., 0.5 to 5 hours).

DETAILED DESCRIPTION OF THE PREFERRED EMBODIMENTS

The process of the present invention is practiced by treating methacrylamidopropyltrimethylammonium chloride in aqueous solution with hydrophobic/organophilic microporous crystalline silica. Although the treatment may be conducted by batchwise processes, it is preferably conducted on a continuous basis.

The process of the present invention is conducted in conventional equipment, such as an autoclave for batch treatment, or in a continuous treating vessel provided with a bed of the hydrophobic/organophilic microporous crystalline silica by bringing a stream comprising methacrylamidopropyltrimethylammonium chloride into contact with the hydrophobic/organophilic microporous crystalline silica for a period of time to significantly lower the level of impurities in the product. Although there is no upper limit to the amount of hydrophobic/organophilic microphorous cyrstalline silica that can be used, economics will dictate the use of as small an amount as is reasonably possible. Successful results have been obtained with ratios of hydrophobic/organophilic microphorous crystalline silica to methacrylamidopropyltrimethylammonium chloride as low as 0.02 grams of silica per gram of chloride. Suitably, the range will be from about 0.02 to about 0.1 gram of silica per gram of chloride.

The process of the present invention is suitably conducted at ambient temperatures although higher or lower temperatures may be used. Thus, temperatures in the range of about 50° to 150° C. may be employed.

Contact times will vary depending upon the method of treatment. Thus, in a continuous process, the contact will be measured in terms of the volumes of feed per volume of silica bed per hour. On this basis, the flow rate should be from about 0.1 to about 1 vol./hr./vol. of silicate.

On a batch basis, the amount of the hydrophobic/organophilic microporous crystalline silica that is used may be from about 0.1 to about 0.02 grams per gram of methacrylamidopropyltrimethylammonium chloride.

It has also been discovered that hydrophobic/organophilic microporous crystalline silica that has become at least partially ineffective through use in the purification of methacrylamidopropyltrimethylammonium chloride can be regenerated by withdrawing the silica from service and treating it with $C_1$–$C_4$ aliphatic alcohol or a $C_5$–$C_8$ alkene such as methanol, ethanol, propanol, butanol, pentene, hexene, heptene or octene. The treatment is accomplished by contacting the spent silica, preferably at atmospheric pressure, with about 5 to 50 parts by weight of the alcohol or alkene per part of spent silica at a temperature within the range of about 50° to about 200° C. (e.g., at the boiling point of the alcohol or alkene) for a period of time, normally within the range of about 0.5 to 5 hours (depending on the level of contamination of the silica, the amount of alcohol or alkene used and the temperature) sufficient to cause the impurities to become disengaged from the silica. Thereafter, the silica may be washed with an additional quantity of alcohol or alkene, if desired, and then dried for return to service.

Although the regeneration process is preferably conducted at atmospheric pressure, higher or lower pressures may be used, if desired, with an appropriate adjustment of the regeneration temperature consistent with the regeneration pressure to be utilized.

EXAMPLE 1

In order to demonstrate the ability of the hydrophobic/organophilic microporous crystalline silica to remove impurities, a series of tests were run utilizing Union Carbide Silicalite/115 as the hydrophobic/organophilic microporous crystalline silica. An impure sample of methacrylamidopropyltrimethylammonium chloride was used as the feed. Three comparative tests were conducted, with the results that are set forth in the following table:

TABLE I

|  | TEST NO. | | | | | |
|---|---|---|---|---|---|---|
|  | 1 | | 2 | | 3 | |
|  | g Silicalite/g MAPTAC[1] | | | | | |
|  | 0.1 | | 0.1 | | 0.091 | |
|  | MAPTAC Sample | | | | | |
|  | Before Treatment | After Treatment | Before Treatment | After Treatment | Before Treatment | After Treatment |
|  | | | Sample N.B. No. | | | |
| MAPTAC Analysis: | 5614-7-3 | 5614-7-8 | 422-11-0382 | 5614-15-13 | 422-1-0181 | 5614-17-8 |
| AMA[2] by LC, ppm | 41.1 | 1.5 | 2.8 | <2 | 41.1 | <2 |
| MEHQ[3] by LC, ppm | 628.5 | 150.8 * | 739 | 95.3 | 628.5 | 91.2 |
| MA[4] by LC, ppm | 1592 | 51.9 | 1392 | 149.4 | 1592 | 404 |
| Gardner Color | ~7 | 7-8 | ~5 | ~5 | ~7 | ~7 |
| H$_2$O, %, KF | 50.4 | 45.7 - | 49.6 | | 50.4 | 49.6 |
| Ref. Index, 25° C. | 1.4271 | 1.4368 | 1.4279 | 1.4329 | 1.4271 | 1.4309 |

[1]MAPTAC = Methacrylamidopropyltrimethylammonium chloride
[2]AMA = Allylmethacrylate
[3]MEHQ = The methylether of hydroquinoe
[4]MA = Methacrylic acid In conducting the tests the Silicalite and the MAPTAC were mixed for four hours at room temperature, then the MAPTAC product was recovered by filtration.

Repetitive treatments of the fresh MAPTAC with the same sample of Silicalite indicated that acceptable allyl methacrylate removal was possible at net ratios as low as 0.02 grams of Silicalite per gram of MAPTAC.

It will be seen from Table I that in all instances the removal of allyl methacrylate was almost complete and that there was a very significant reduction in impurity levels for the methylether of hydroquinone (an oxidation inhibitor) and methacrylic acid.

EXAMPLE 2

In order to test the capacity of Silicalite for impurity removal, about 20 grams of Silicalite was treated batchwise as described in Example 1 with sequential 200 gram samples of MAPTAC. The results of this series of ten tests is set forth in Table II.

TABLE II

| Treatment # | Total Accumulated g MAPTAC/ g Silicalite | N.B. # 5614- | MAPTAC Analysis | | | Color Gardner | Reference Index |
|---|---|---|---|---|---|---|---|
| | | | AMA ppm | MEHQ ppm | MA ppm | | |
| 0 | | (422-1-0181) | 41.1 | 628.5 | 1592 | ≅7 | 1.4309 |
| 1 | 200 | 17-17 | <2 | 88.6 | 244 | ≅7 | 1.4425 |
| 2 | 400 | 17-28 | <2 | 487 | 2099 | ≅6 | 1.4428 |
| 3 | 600 | 17-35 | 2.9 | 581 | 2779 | ≅7 | 1.4405 |
| 4 | 800 | 19-4 | <2 | 659 | 2796 | ≅7 | 1.4398 |
| 5 | 1000 | 19-11 | 3.8 | 654 | 2922 | ≅7 | 1.4542 |
| 6 | 1200 | 19-15 | 21.35 | 685.3 | 2888 | ≅7 | 1.4385 |
| 7 | 1400 | 19-20 | 25.6 | 701.7 | 2746 | ≅7 | 1.4455 |
| 8 | 1600 | 19-26 | 37.6 | 675 | 2736 | ≅7 | 1.4449 |
| 9 | 1800 | 19-30 | 41.8 | 697 | 3007 | ≅7 | 1.4437 |
| 10 | 2000 | 19-35 | 41 | 682 | 2975 | ≅7 | 1.4462 |

The amount of MAPTAC treated in the sequential treatments as shown in column 2 is cumulative. Note that the 20 gram sample of Silicalite was used to successfully treat 1000 grams total of MAPTAC at a net ratio of 50 grams total MAPTAC per gram Silicalite, (treatments 1-5) before significant quantities of impurities remained in the product.

EXAMPLE 3

A feature of the present invention is a continuous process involving regeneration of the spent hydrophobic/organophilic microporous crystalline silica after it has become saturated by the removal of impurities from impure methacrylamidopropyltrimethylammonium chloride. A portion of Silicalite was used at a ratio of 0.0217 grams Silicalite per gram MAPTAC in order to exhaust the ability of the Silicalite to absorb AMA and methacrylic acid. The "spent" Silicalite was then divided into equal portions, and each of the portions was treated in a different boiling solvent for 4 hours at a ratio of 25 grams solvent/gram Silicalite. An agitator and total reflux condenser were utilized in this step. The solvent was discarded, and the above wash step was repeated with new solvent. The Silicalite portions were then "dried" for 8 hours in a 55° C. oven, then tested by treating MAPTAC containing a relatively high level of AMA impurities at a weight ratio of about 0.09 grams "regenerated" Silicalite per gram MAPTAC. Results shown in the table below show analyses of MAPTAC samples after the above regeneration attempts. Regeneration by boiling methanol appears to be the most promising solvent tested to date. The recovered MAPTAC from the methanol washed, regenerated Silicalite was significantly lower in MEHQ and methacrylic acid content than the MAPTAC obtained from the other washes and was as good as new Silicalite in AMA removal ability. Only the cyclohexane "regenerated" Silicalite treated MAPTAC was higher in AMA content than the new Silicalite treated MAPTAC, thus demonstrating the suitability of $C_1$–$C_4$ aliphatic alcohols and $C_5$–$C_8$ alkenes for use in the regeneration of "spent" Silicalite.

TABLE III

|  | None-Starting MAPTAC | Regeneration Solvent | | | |
|---|---|---|---|---|---|
|  |  | None-Treated with New Silicalite | Cyclohexane | Methanol | Hexene |
| MAPTAC Analysis: | 422-1-0181 | 5614-7-8 | N.B. No. 5614-35-9 | 5614-35-29 | 5614-35-26 |
| AMA by LC, ppm | 41.1 | 1.5 | 13.6 | <2 | <2 |
| MEHQ by LC, ppm | 628 | 150.8 | 664.1 | 165 | 539.5 |
| MA by LC, ppm | 1592 | 51.9 | 2234.9 | 1245 | 2053 |
| Gardner Color | ~7 | 7–8 | ~7 | ~8 | ~7 |
| H₂O, K.F., % | 50.4 | 45.7 | 46.3 |  |  |
| Ref. Index, 25° C. | 1.4271 | 1.4368 | 1.4402 | 1.4662 | 1.4377 |

TABLE IV

| Lot No. | AMA, ppm | Homopolymer Viscosity cpxd |
|---|---|---|
| 422-35-1080 | 107 | 8.0 |
| 422-8-1180 | 75 | 7.7 |
| 422-8-0980 | 35 | 8.6 |
| 422-8-1180B | 15 | 8.7 |
| 422-8-1180B | <10 | 9.0 |
| 422-14-0780 | 6.6 | 9.02 |

The above examples are given by way of illustration only and are not intended as limitations on the scope of this invention, which is defined by the appended claims.

What is claimed is:

1. A method for the purification of an impure methacrylamidopropyltrimethylammonium chloride which comprises contacting an aqueous solution of said impure chloride with hydrophobic/organophilic microporous crystalline silica for a period of time sufficient to significantly lower the impurities level, said microporous crystalline silica having a topological tetrahedral framework characterized by straight channels along a b-axis defined by ten membered oxygen rings with an elliptical cross-section of 5.7–5.8 Å by 5.1–5.2 Å interconnected by zigzag channels along an a-axis defined by ten membered oxygen rings with an aporoximately circular cross-section of about 5.4±2 Å.

EXAMPLE 4

A measure of the adverse affect of impurities on the polymerization of methacrylamidopropyltrimethylammonium chloride is a measurement of the viscosity of a high molecular weight homopolymer prepared from the monomer.

In order to illustrate this, methacrylamidopropyltrimethylammonium chloride from different batches of product having different levels of contamination with allylmethacrylate were polymerized.

The polymerization procedure that was used was as follows: about 200 gm of a 50% aqueous solution of methacrylamidopropyltrimethylammonium chloride, 134 gm of deionized water, 0.500 gm of 2,2'acobis(2-amidinopropane) hydrochloride and 0.110 gm of sodium silicylate were combined in a glass polymerization vessel. The solution was purged with nitrogen for one hour with agitation and then heated at 50° C. with agitation in an atmosphere of nitrogen for about 5.67 hours. The product was then removed, cooled and viscosity was measured with a vibrating sphere viscometer at 25° C. using a sample composed of 5 gm of the polymer product in 295 gm of deionized water.

The homopolymers formed as a result of the polymerization were then tested for viscosity and the results of this test are recorded in Table IV. As will be seen from Table IV, the homopolymers having the lowest level of allyl methacrylate contamination have the highest viscosity.

2. A method as in claim 1 wherein the process is conducted on a continuous basis by passing the methacrylamidopropyltrimethylammonium chloride through a bed of the hydrophobic/organophilic microporous crystalline silica at a temperature of about 50° to about 150° C. at a space velocity of about 0.1 to about 1 volume of said chloride per hour per volume of said silica.

3. A method as in claim 1 wherein the process is conducted on a batch basis by contacting a batch of the impure methacrylamidopropyltrimethylammonium chloride with from about 0.1 to about 0.02 grams of hydrophobic/organophilic microporous crystalline silica per gram of impure chloride at a temperature of about 50 to about 150 for a period of time within the range of about 0.5 to about 5 hours and thereafter filtering the resultant product to remove the hydrophobic/organophilic microporous crystalline silica from the thus purified methacrylamidopropyltrimethylammonium chloride.

4. A regenerative process for the purification of impure methacrylamidopropyltrimethylammonium chloride which comprises contacting the impure methacrylamidopropyltrimethylammonium chloride contaminated with allyl methacrylate and methacrylic acid with a hydrophobic/organophilic microporous crystalline silica under treating conditions to significantly lower the level of impurities in the said methacrylamidopropyltrimethylammonium chloride to a predetermined purity level and continuing such contact until the said hydrophobic/organophilic microporous crystalline silica is no longer effective for impurity removal to said predetermined impurity level and then:

(a) separating said thus spent hydrophobic/organophilic microporous crystalline silica from the methacrylamidopropyltrimethylammonium chloride, (b) treating said spent hydrophobic/organophilic microporous crystalline silica with an organic solvent effective for contaminant removal for a period of time sufficient to substantially remove the contaminants from the said spent silica, (c) thereafter treating additional quantities of said impure methacrylamidopropyltrimethylammonium chloride with said thus regenerated microporous crystalline silica, (d) said organic solvent being selected from the group consisting of $C_1$–$C_4$ aliphatic alcohols and $C_5$–$C_8$ alkenes, and (e) said microporous crysralling silica having a topological tetrahearal framework characterized by straight channels along a b-axis defined by ten membered oxygen rings with an elliptical cross-section of 5.7–5.8 Å by 5.1–5.2 Å interconnected by zigzag channels along an a-axis defined by ten membered oxygen rings with an approximately circular cross-section of 5.4±0.2 Å.

5. A method as in claim 4 wherein the solvent is a $C_1$–$C_4$ aliphatic alcohol.

6. A method as in claim 5 wherein the polar organic solvent is methanol.

7. A method as in claim 4 wherein the organic solvent is a $C_5$–$C_8$ unsaturated aliphatic hydrocarbon.

8. A method as in claim 7 wherein the unsaturated aliphatic hydrocarbon solvent is hexene.

* * * * *